United States Patent [19]

Compans

[11] Patent Number: 5,550,017

[45] Date of Patent: Aug. 27, 1996

[54] ANTI-PARAMYXOVIRUS SCREENING METHOD AND VACCINE

[75] Inventor: Richard W. Compans, Atlanta, Ga.

[73] Assignee: Emory University, Atlanta, Ga.

[21] Appl. No.: 135,285

[22] Filed: Oct. 12, 1993

[51] Int. Cl.$^6$ .................................................. C12Q 1/70
[52] U.S. Cl. ........................... 435/5; 435/7.21; 436/545; 436/804
[58] Field of Search ..................... 435/5, 7.21; 514/12; 436/804, 545

[56] References Cited

U.S. PATENT DOCUMENTS

| | | | |
|---|---|---|---|
| 4,790,987 | 12/1988 | Compans | 424/89 |
| 5,169,628 | 12/1992 | Wathen | 424/186.1 |

OTHER PUBLICATIONS

Hu, X. et al. (1992), "Functional Interactions between the Fusion Protein and Hemagglutinin–Neuraminidase of Human Parainfluenza Viruses," *J. Virol.* 66:1528–1534.

Morrison, T. et al. (1991), "Complementation between Avirulent Newcastle Disease Virus and a Fusion Protein Gene Expressed from a Retrovirus Vector: Requirements for Membrane Fusion," *J. Virol.* 65:813–822.

Katzir, Z. et al. (1989), "Application of Fluorescene Photobleaching Recovery to Assess Complex Formation between the Two Envelope Proteins of Sendai Virus in Membranes of Fused Human Erythrocytes," *Biochemistry* 28:6400–6405.

Ebata, S. N. et al. (1991), "The Fusion and Hemagglutinin–Neuraminidase Glycoproteins of Human Parainfluenza Virus 3 are both Required for Fusion," *Virology* 183:437–441.

Matsuoka, Y. et al. (1990), "Sequence of the Hemagglutinin–Neuraminidase Gene of Human Parainfluenza Virus Type 1," *Virus Res.* 16:107–113.

Blumberg, B. et al. (1985), "Sequence Determination of the Sendai Virus HN Gene and its Comparison to the Influenza Virus Glycoproteins," *Cell* 41:269–278.

Elango, N. et al. (1986), "Human Parainfluenza Type 3 Virus Hemagglutinin–Neuraminidase Glycoprotein: Nucleotide Sequence of mRNA and Limited Amino Acid Sequence of the Purified Protein," *J. Virol.* 57:481–489.

Merson, J. R. et al. (1988), "Molecular Cloning and Sequence Determination of the Fusion Protein Gene of Human Parainfluenza Virus Type 1," *Virology* 167:97–105.

Millar, N. S. et al. (1986), "Nucleotide Sequence Analysis of the Haemagglutinin–Neuraminidase Gene of Newcastle Disease Virus," *J. Gen. Virol.* 67:1917–1927.

Fuerst, et al. (1986), "Eukaryotic Transient–Expression System Based on Recombinant Vaccinia Virus that Synthesizes Bacteriophage T7 RNA Polymerase," *Proc. Nat'l. Acad. Sci. USA* 83:8122–8126.

Markwell, M. A. K. and Fox, C. F. (1980), "Protein–Protein Interactions within Paramyxoviruses Identified by Native Disulfide Bonding or Reversible Chemical Cross–Linking," *J. Virol.* 33:152–166.

Sechoy, O. et al. (1987), "F Protein–F Protein Interaction within the Sendai Virus Identified by Native Bonding or Chemical Cross–Linking," *J. Biol. Chem.* 262:11519–11523.

Scheid, A. and Choppin, P. W. (1974), "Identification of Biological Activities of Paramyxovirus Glycoproteins. Activation of Cell Fusion, Hemolysis, and Infectivity by Proteolytic Cleavage of an Inactive Precursor Protein of Sendai Virus," *Virology* 57:475–490.

Homma, M. and Ohuchi, M. (1973), "Trypsin Action on the Growth of Sendai Virus in Tissue Culture Cells," *J. Virol.* 12:1457–1465.

Citovsky, V. et al. (1986), "The Use of Circular Dichroism to Study Conformational Changes Induced in Sendai Virus Envelope Glycoproteins," *J. Biol. Chem.* 261:2235–2239.

Nakanishi, M. et al. (1982), "Glycoproteins of Sendai Virus (HVJ) have a Critical Ratio for Fusion between Virus Envelopes and Cell Membranes," *Exp. Cell Res.* 142:95–101.

Roux, L. (1990), "Selective and Transient Association of Sendai Virus HN Glycoprotein with BiP," *Virology* 175:161–166.

Ray, R. et al. (1985), "Glycoproteins of Human Parainfluenza Virus Type 3: Characterization and Evaluation as a Subunit Vaccine," *J. Infect. Dis.* 152:1219–1230.

Ray, R. et al. (1988), "Role of Individual Glycoproteins of Human Parainfluenza Virus Type 3 in the Induction of a Protective Immune Response," *J. Virol.* 62:783–787.

Ray, R. et al. (1988), "Intranasal Immunization of Hamsters with Envelope Glycoproteins of Human Parainfluenza Virus Type 3," *J. Infect. Dis.* 157:648–654.

Ray, R. et al. (1990), "Human Parainfluenza Virus Induces a Type–Specific Protective Immune Response," *J. Infect. Dis.* 162:746–749.

Taylor, J. et al. (1991), "Vaccinia Virus Recombinants Expressing either the Measles Virus Fusion or Hemagglutinin Glycoprotein Protect Dogs against Canine Distemper Virus Challenge," *J. Virol.* 65:4263–4274.

Joklik et al., Eds., *Zinsser Microbiology*, 20th Edition, Appleton & Lange, Norwalk, 1992, pp. 1002–1005.

*Primary Examiner*—Toni R. Scheiner
*Assistant Examiner*—Donna C. Wortman
*Attorney, Agent, or Firm*—Greenlee and Winner PC

[57] ABSTRACT

A method is provided for detecting whether a test composition can inhibit cell fusion mediated by paramyxovirus infection. A method is also provided for identifying an antiviral peptide capable of inhibiting paramyxovirus-induced cell fusion. The methods are based on the discovery that the hemagglutination and fusion-inducing proteins of paramyxoviruses interact to form a complex termed HN:F, that is prerequisite to cell fusion. Antibodies to HN:F provide a novel means of providing improved immunity against paramyxovirus infection.

4 Claims, 6 Drawing Sheets

Schematic diagrams of chimeric proteins encoded by chimeric PI2 - SV5 HN genes

FIG. 4

Parainfluenza 2 virus HN gene restriction map.

```
       DraI  NsiI  Eco57I BglII FauI FokI      EcoRI         HhaI
       308   320   627    748  886  983        1289          1540
    0   |    |     |      |    |    |           |             |         1713
    ────┼────┼─────┼──────┼────┼────┼───────────┼─────────────┼──────────
        ┬          ┬           ┬               ┬             ┬
```

Simian virus 5 HN gene restriction map.

```
       PstI  BsiI       GsuI        HgiAI       AflIII   HgiEII BsaBI NruI ThaI
       239   332        751         904         1180     1771   1500  1506 1506
    0   |    |          |           |            |        |      |    ||        1695
    ────┼────┼──────────┼───────────┼────────────┼────────┼──────┼────┼┼────────
        ┬               ┬           ┬            ┬        ┬
```

ANTI-PARAMYXOVIRUS SCREENING METHOD AND VACCINE

FIELD OF INVENTION

The invention relates to viruses, specifically paramyxoviruses, including structural aspects of virus components and methods of therapy and prevention of virus infection.

BACKGROUND AND PRIOR ART

The paramyxoviruses infect both humans and animals. The group includes well-known human pathogens such as parainfluenza viruses of which several types are known, measles virus, mumps virus, and respiratory syncytial virus. Among the animal-pathogenic paramyxoviruses are canine distemper virus, rinderpest virus, and Newcastle disease virus. The paramyxoviruses are single-stranded RNA viruses. The virus particles have an outer membrane with short projecting spikes, and an inner nucleocapsid. The spikes include two glycoproteins of relevance, a hemagglutinin with neuraminidase activity (HN) and a cell fusion-inducing protein (F).

Pathogenesis and virus spread through the infected host are both facilitated by virus-mediated cell fusion. Recent work has demonstrated that both HN and F are required for cell fusion to occur [Hu, X. et al. (1992) *J. Virol.* 66:1528–1534; Morrison et al. (1991), *J. Virol.* 65:813–822; Katzir, Z. et al. (1989) *Biochemistry* 28:6400–6405; Ebata, S. N. et al. (1991) *Virology* 183:437–441]. The genes encoding HN and F, respectively, have been cloned from several virus types, including Sendai (SN), simian virus 5 (SV5) parainfluenza type 1 (PI1), parainfluenza type 2 (PI2), and parainfluenza type 3 (PI3). The respective proteins have been purified and various polyclonal and monoclonal antibodies against them have been obtained. Substantial sequence differences exist between the respective HN and F proteins of SN, PI1, PI2, and PI3, although the greatest sequence similarities exist between SN and PI1 [Matsuoka, Y. et al. (1990) *Virus Res.* 16:107–114; Blumberg, B. et al. (1985) *Cell* 41:269–278; Elango, N. et al. (1986) *J. Virol.* 57:481–489; Merson, J. R. et al. (1988) Virology 167:97–105; Millar, N. et al. (1986) *J. Gen. Virol.* 67:1917–1927]. HN and F can be expressed either individually or together in HeLa-T4 cells using a vaccinia-T7 recombinant virus vector system [Fuerst, et al. (1986) *Proc. Nat'l. Acad. Sci. USA* 83:8122–8126].

Various experimental approaches have been taken in an attempt to further define the respective roles of HN and F in cell fusion. The possibility of direct association of HN and F has been considered, however, the evidence to date has been negative. Initial studies by Markwell, M. A. K. and Fox, C. F. (1980) *J. Virol.* 33:152–166 demonstrated that HN of Sendai and Newcastle disease viruses exists as a disulfide linked homodimer. The authors also studied spatial relationships of viral proteins by observing the effects of chemical cross-linking reagents on proteins of the mature virus. Interactions up to 1.1 nm distance were expected to be detectable. The NP (nucleoprotein) and M (membrane) proteins were cross-linked by the reagents. Also the F protein could be cross-linked to itself, suggesting that F exists in the native virus as noncovalent homo-oligomers. No close association between HN and F was observed in the cross-linking studies. Sechoy, O. et al. (1987) *J. Biol. Chem.* 262:11519–11523 extended the previous study with respect to F, using a system of purified F in reconstituted lipid vesicles. The authors concluded that native F exists as a noncovalent association of homo-tetramers, each consisting of two peptides, $F_1$ and $F_2$, linked by a disulfide bond. ($F_1$ and $F_2$ are formed by posttranslational cleavage of a precursor, $F_0$ [Scheid, A. and Choppin, P. W. (1974) *Virology* 57:475–490; Homma, M. and Ohuchi, M. (1973) *J. Virol.* 12:1457–1465]. Citovsky, V. et al. (1986) *J. Biol. Chem.* 261:2235–2239 studied HN and F in reconstituted lipid vesicles by circular dichroism. HN and F were purified from detergent-extracted virus particles. The circular dichroism spectrum of vesicles reconstituted with both HN and F was shifted with respect to the spectra of vesicles reconstituted with HN or F alone. The authors inferred a changed conformation of the glycoproteins of the HN-F vesicles, possibly as the result of action of HN upon F. Nakanishi, M. et al. (1982) *Exp. Cell Res.* 142:95–101 also studied purified HN and F in reconstituted vesicles, using diphtheria toxin A fragment to confer cytotoxicity on the vesicles and varying proportions of HN and F. Optimum cytotoxicity of the vesicles was observed when the ratio of F to HN was two. Roux, L. (1990) *Virology* 175:161–166 studied the interaction of HN and F with the immunoglobulin heavy chain binding protein (BiP) by measuring the amount of HN or F precipitated by a monoclonal antibody to BiP. BiP belongs to the heat shock family. It is proposed to function as a "chaperon" protein to aid in maintaining proper folding of other nascent proteins during maturation. Anti-BiP antibody was found to precipitate HN in infected cells, along with BiP, however, only one-fifth as much F was coprecipitated as HN. Katzir, Z. et al. (1989) *Biochemistry* 28:6400–6405 set out specifically to test whether F-HN complexes are formed in infected cell membranes. The authors measured fluorescence photobleaching recovery as a measure of each component's lateral mobility in the membrane. One component was immobilized with an antigen and the effect on mobility of the other, labeled with a fluorophore, was investigated. The authors did not find any effect of HN on lateral mobility of F, or vice-versa, suggesting that no HN-F complexes formed. For a general review, see Morrison T. and Portner, A. (1991) Structure, function and processing of the glycoproteins of Paramyxoviridae, In *The Paramyxoviruses* (D. W. Kingsbury ed.) Plenum Publishing Co., New York, pp. 347–382.

SUMMARY OF THE INVENTION

The present invention includes a method for detecting whether a test composition can inhibit cell fusion mediated by paramyxovirus infection. The method is based on the discovery that the HN and F glycoproteins of paramyxoviruses interact with one another to form a complex, termed an "HN:F complex" or simply "HN:F" herein, that can be isolated, and that HN:F complex formation is a prerequisite for cell fusion. Accordingly, by measuring the amount of HN:F complex formed in the membranes of transformed host cells expressing type-homologous HN and F proteins in the presence and absence of various test compositions, the effectiveness of such compositions to inhibit virus-mediated cell fusion can be measured. The term "type-homologous" is used herein to denote that the HN and F components are of the same virus type. As disclosed herein, HN:F complexes are not formed if the HN and F components are of different virus type, except for PI1 and SN, which are defined as "type-homologous." Any pair of virus strains are type-homologous if they can form hetero-HN:F complexes with one another and are not type-homologous if they cannot.

Another aspect of the invention is a consequence of the fact that antibody specificity of an HN:F complex differs from that of either HN or F alone. Novel antibodies to an HN:F complex exert a unique protective effect by interfering with cell fusion and cell-cell virus transfer. The invention therefore provides a novel antigen and vaccine produced therefrom to provide more complete immunity against paramyxoviruses than was available heretofore.

BRIEF DESCRIPTION OF THE FIGURES

FIG. 3(A,B,C) is a micrograph showing capping and cocapping of F and HN proteins as described in Example 3. The results are shown in double exposure with the field moved slightly to show: A) a capped cell (left) and an uncapped cell (right); B) FITC fluorescence used to label HN (right) and RITC fluorescence used to label F (left) on the same capped cell; C) FITC fluorescence used to label PI2 HN under capping conditions (left) and RITC fluorescence used to label PI3 F under noncapping conditions (right), on the same cell.

DETAILED DESCRIPTION OF THE INVENTION

The paramyxoviruses are unique in having both a fusion protein (F) and a hemagglutinin-neuraminidase protein (HN). (In one subgroup, the morbilliviruses, neuraminidase activity is lacking in the hemagglutinin protein). The cell fusions caused by these viruses are the result of activities of the HN and F proteins, or their counterparts. The experiments described herein have been performed with strains of parainfluenza viruses and the closely homologous Sendai virus. The findings described herein, and their applications, will be understood to apply to any paramyxovirus and thus to have application to the entire range of paramyxovirus diseases of animals and humans.

The abbreviation "HN" is used herein to signify the paramyxovirus hemagglutinin-neuraminidase glycoprotein or its morbillivirus counterpart. The HN glycoprotein genes of several paramyxoviruses have been cloned and sequenced.

The abbreviation "F" is used herein to signify the fusion protein of paramyxoviruses. Several F glycoprotein genes of different paramyxovirus strains have been cloned and sequenced.

The abbreviation "HN:F" denotes the complex, newly discovered as a facet of the present invention, which is formed in naturally infected cells or in cells transformed with DNA encoding HN and F. As detailed herein, the HN:F complex can be immunoprecipitated by antibody to either of its components, HN or F. The HN:F complex is disrupted by conditions of SDS-PAGE, suggesting that the complex is not stabilized by a covalent bond between the HN and F moieties. Further, an HN:F complex is only formed between type-homologous components, as herein defined. For example, HN of parainfluenza type 2 (PI2-HN) can form an HN:F complex with F glycoprotein of the same type (PI2-F) but not with F of a different type, e.g., PI3-F. The same holds for reciprocal combinations and for all combinations tested, in both naturally infected cells and transformed cells. The formation of an HN:F complex correlates completely with cell fusion. Cell fusion only occurs under conditions where HN:F complex formation occurs. Conversely, no cell fusion occurs under conditions where HN:F complex formation does not occur, for example, where host cells are cotransformed with PI2-HN and PI3-F. Therefore, HN:F is required for cell fusion.

Type-specificity of the paramyxoviruses has been classified by immunological characteristics, which are conferred by the distinct antigens of the virus: HN, F and an internal nucleocapsid protein termed NP. Other distinctions, such as host-range or nature of pathogenic symptoms have resulted in certain related viruses having received different names. For example, when amino acid sequences of their HN and F proteins are compared, SV5 and PI2 are seen to be more closely related to one another than to other parainfluenza types. Therefore, for the purposes herein, "type-specificity" is used to include any criterion applied to paramyxoviruses by which the viruses are distinguished from one another.

"Type-homologous" is the term used herein to express the relationship of virus strains which are so closely homologous as to permit mixed HN:F complexes to form upon mixed infection or cotransformation. Only one example is presently known. Sendai virus and PI1 are type-homologous. These two strains also have the most closely homologous HN and F glycoprotein amino acid sequences of any of the paramyxoviruses for which data is available. Other such closely related, type-homologous strains may, of course, exist. They will be readily recognizable by their ability to form HN:F complexes upon mixed infection or cotransformation.

In certain of the procedures described herein, proteins are identified by means of a label which provide sufficient sensitivity to detect and/or measure the small amounts of proteins produced. Any material that can provide the requisite sensitivity, incorporated into the glycoprotein either during translation or posttranslationally can be employed as a matter of choice by those skilled in the art who practice the invention. The examples herein employ methionine labeled with a sulfur isotope, $^{35}S$, as a convenient precursor label. Nevertheless, the terms "label" and "labeling" are to be construed as including such other labels as may be known to those skilled in the art. A "labeled protein precursor" means a labeled amino acid or amino acid precursor which becomes incorporated into protein in the course of cell metabolism.

An HN:F complex includes two components, a first component which may be designated either as HN or F, and a second component, which is the remaining component, either HN or F depending on which of the two is designated as the first component. It is convenient to isolate HN:F by a specific binding agent, such as an antibody, able to combine preferentially with one of the two components, or to the HN:F complex. If the complex is isolated by means of an antibody to a first component, the amount of complex can be quantitatively measured by means of a reagent, such as a labeled antibody, which specifically binds the second component. The subfraction that is isolated by antibody to the first component contains both HN:F and any free, noncomplexed first component which may exist, but any free, unbound second component remains behind. If HN:F is isolated by means of a reagent, such as an antibody specific for the HN:F, the free, noncomplexed first and second components are left behind. The amount of HN:F complex can then be measured by a labeled reagent, such as an antibody, specific for either of the components.

Being able to measure the amount of HN:F complex formed under various conditions, for example, in the presence and absence of a putative inhibitor of HN:F complex formation, provides a means for screening potential antiviral agents. Any compound or composition having the ability to either prevent HN:F complex formation or disrupt preexisting HN:F complexes can inhibit virus-induced cell fusion and thereby function as an antiviral agent. By comparing the amount of HN:F complex in the presence and absence of a test composition, one can detect whether a given test composition inhibits formation of an HN:F complex of a given paramyxovirus strain or type-homologous strains. It will be understood that it does not matter, from a practical standpoint, whether the inhibitor acts by preventing initial formation of the HN:F complex or by disrupting a complex after it is formed, since the measured result is a reduced amount of HN:F when inhibitor is present, compared to when it is absent. Therefore, the terms "inhibitor" and "inhibitor of HN:F complex formation" are not intended to imply any mechanism by which the amount of HN:F is reduced. Furthermore, it will be understood that a given inhibitor may be specific to type-homologous virus strains, or it may have a broader spectrum of activity.

Another consequence of the finding that an HN:F complex forms in infected cells or in cells cotransformed with type-homologous HN and F coding sequences of DNA is that the complex is a novel antigen. Novel antibodies directed against the HN:F complex can be raised. Such anti-HN:F antibodies can be polyclonal or monoclonal. Antibodies to HN:F inhibit the activity of HN:F in promoting cell fusion and intracellular virus transfer. Consequently, HN:F complexes form the basis of a novel type of subunit vaccine against type-homologous virus strains. HN:F can be used either alone or in combination with other viral antigens, such as HN and F, to generate protective antibodies to type-homologous virus infection. Labeled anti-HN:F antibody is also useful as a quantitative reagent for detecting, localizing, and measuring HN:F.

The finding that HN:F is only formed between type-homologous HN and F provides a strategy for identifying an antiviral peptide. The strategy in essence involves mapping the peptide domains of HN and F which interact to form an HN:F complex and maintain its stability. Since HN and F of different type specificity do not form HN:F, it is possible to use chimeric HN or chimeric F proteins, between HN or F proteins, respectively, of different type specificity, to test the type specificity of the chimeras. By testing a series of such chimeras it is possible to define the regions which do not contribute to type specificity in HN:F formation, and those regions which do contribute. The latter include those which interact in the HN:F complex. Oligopeptides comprising an amino acid sequence of a peptide region of HN or F that contributes to type specificity is likely to act as an inhibitor of HN:F formation. Such oligopeptides can be synthesized chemically or biologically (by transforming a cell with a DNA encoding the oligopeptide). Testing for the ability of a given peptide to inhibit HN:F formation is a straightforward application of the methods described herein for demonstrating the existence of HN:F. A direct test is one which measures HN:F, for example, by immunoprecipitation, while an indirect test is one which measures cell fusion caused by the presence of functional HN:F, for example, cell fusion or capping/cocapping analysis.

The experimental details are given in the Examples which show: (Example 1) that HN:F can be immunoprecipitated by antiserum to HN; (Example 2) that HN:F complexes are membrane-localized; (Example 3) that the HN and F proteins comigrate in cell membranes; that the quantity of HN:F formed in the presence or absence of divers test compositions forms the basis of a test for anti-paramyxovirus agents; (Example 4) that antibodies specifically directed to the HN:F complex can be raised; and (Example 5) that HN:F preparations provide the basis for an anti-paramyxovirus vaccine. Example 6 describes techniques for mapping peptide domains of HN or F that interact in HN:F formation. Many of the techniques and materials upon which the Examples are based are described below.

Viruses and Cells. PI2 and PI3 viruses were obtained from the Division of Research Resources, National Institutes of Health, Bethesda, MD. The viruses were grown on LLC-$MK_2$cells as described previously (Hu et al., 1992). The vaccinia-T7 recombinant virus (WR strain) was obtained from Dr. Bernard Moss. HeLa-T4 and HeLa cells were purchased from the American Type Culture Collection (ATCC), Rockville, Md. Cells were grown in Dulbecco's modified Eagle's medium containing 10% defined/supplemented newborn calf serum (Hyclone Laboratories, Inc., Logan, Utah).

Recombinant Plasmids. PI2-F and HN cDNA genes were cloned in pGEM-3 and pGEM-3Zf(−) plasmids (Promega Biotech, Madison, Wis.), respectively, at the Sma I site as described previously (Hu et al., 1992). The PI3 F and HN cDNA clones were kindly provided by Dr. Mark Galinski. These two genes were subcloned into pGEM plasmid vectors. The pGEM-4-SNF and pGME-4-SN HN cDNA clones were kindly provided by Dr. Laurent Roux. The SV5-F and -HN cDNA clones were kindly provided by Dr. Robert A. Lamb and were subcloned in pGEM plasmids. The PI1-HN cDNA gene was obtained from Dr. Yumiko Matsuoka and was subcloned in pGem-4.

Rabbit Antisera. Rabbit antisera against PI1 or PI3 viruses were produced as described previously (Hu et al., 1992). Rabbit antisera against PI2-HN and PI3-HN were generated as described by Ray and Compans (1987). Rabbit antiserum against Sendai virus was kindly provided by Dr. Laurent Roux. Rabbit antiserum against SV5 virus was kindly provided by Dr. Robert A. Lamb.

Infection and Transfection. Infection of cells with paramyxoviruses was performed as previously described (Hu et al., 1992). For the vaccinia-T7 expression system, confluent monolayers of cells grown in 35-mm dishes were infected with the vaccinia-T7 recombinant (Fuerst et al., 1986, supra) at a M.O.I. of 10 and incubated at 37° C. for 45 min. Cells were carefully washed with phosphate-buffered saline (PBS) 3 times and then transfected with 5 mg of plasmid DNA and 20 ml of cationic liposomes in 2 ml of Dulbecco's modified Eagle's medium. Cationic liposomes were prepared according to the procedure of Rose et al. (1991) *BioTechniques* 10:520–525: 2 mg of dimethyldiotadecylammonium bromide (DDAB) (SIGMA, St. Louis, Mo.) was dissolved in 5 mg of 10 mg/ml dioleoyl-L-a-phosphatidylethanolamine (PtdEtn) (SIGMA), dried in a speed vacuum concentrator and resuspended in 5 ml of sterile distilled water by sonication. Dulbecco's modified Eagle's medium with or without 5% newborn calf serum was added after cells were incubated with the transfection mixture at 37° C. for 5 h. Immunoprecipitation assays were performed 12 to 16 h posttransfection.

Radiolabeling and Immunoprecipitation. Twelve hours post-transfection, cells were starved in Dulbecco's modified Eagle's medium lacking methionine and cysteine for 15 min and labeled with 60 mCi of [$^{35}$S]methionine per 35-mm dish for 1 h at 37° C. Immunoprecipitation was performed as described previously (Hu et al., 1992) and the radiolabeled polypeptides were analyzed by SDS-polyacrylamide gel electrophoresis (SDS-PAGE).

Cross-linking. Cross-linking was carried out by a modification of the procedure described by Hamada and Tsuruo (1987). Transfected cells were labeled with [$^{35}$S]-methionine as described above. Cells were incubated with 1 mM dithiobissuccinimidylpropionate (DSP, dissolved in PBS) (Pierce, Rockford, Ill.) on ice for 30 min, and then cross-linkers quenched with Dulbecco's modified Eagle's medium. Cells were lysed with mild lysis buffer (10 mM lauryl maltoside, 100 mM NaCl, mM Hepes, pH 7.3) and the viral proteins were then immunoprecipitated as described above.

Biotinylation Assay. Biotinylation of cell surface proteins was performed as described by [Lisanti et al. (1989) *J. Cell. Biol.* 109:2117–2127]. Briefly, transfected cells were labeled with 100 mCi of [$^{35}$S]-methionine/35-mm dish 10 to 12 hr posttransfection, washed with cold PBS/CM (0.1 mM CaCl$_2$, 1 mM MgCl$_2$ in PBS-D) three times and agitated with PBS/CM on ice for 30 min. After addition of NHS-SS-Biotin (Pierce, Rockford, Ill.) at a concentration of 0.5 mg/ml, cells were incubated on ice with agitation for 15 to 30 min. Cells were then lysed with lysis buffer and antibody was added. After addition of 10 ml of 50% protein A agarose beads and incubation at 4° C. for 2 h, cell lysates were washed with the lysis buffer and 10 ml of 10% SDS was added followed by boiling for 5 min. Supernatants were separated from agarose beads by addition of lysis buffer and centrifugation in a microcentrifuge. Ten ml of 50% Streptavidin agarose beads were added to the supernatant followed by incubation at 4° C. for 2 h. Beads were then washed and boiled, and biotinylated proteins were analyzed by 10% SDS-PAGE.

Capping and Cocapping Assays. HeLa cells were grown in 100-mm cell culture dishes in Dulbecco's modified Eagle's medium with 10% newborn calf serum. Antibody-induced capping was performed as described by Joseph and Oldstone (1974) *J. Immunol.* 113:1205–1209. Briefly, confluent monolayers of cells were infected with PI1 or PI3 virus at a M.O.I. of 5 and incubated at 37° C. for 1 h. Virus-infected cells were then washed with warm PBS-deficient (PBS-D, PBS lacking Mg$^{++}$ and Ca$^{++}$) three times and suspended with 50 mM EDTA at room temperature. Suspended cells were washed and transferred to snaptop tubes in Joklik's medium containing 2% newborn calf serum and incubated at 37° C. for 16 to 20 hr. After cells were washed with ice-cold PBS-D and pelleted by centrifugation at 1,000 rpm, primary antibody to the viral antigen was added followed by incubation on ice for 30 min. Cells were then washed with ice-cold PBS-D and divided into two aliquots. After the secondary antibody conjugated with fluorescein isothiocyanate (FITC) was added, the two aliquots of cells were incubated at 37° C. or 0° C., respectively, for 30 to 60 min. Cells were finally fixed in 1% paraformaldehyde and resuspended in 200 ml of PBS-D for fluorescence microscopy.

Cocapping analysis was carried out by adding primary antibody to the second antigen and secondary antibody conjugated with rhodamine isothiocyanate (RITC) with each incubation interval for 30 min on ice. Cells were washed with cold PBS-D and pelleted at 1,000 rpm after each incubation. Fluorescence microscopy was performed by using two different fluorescence filters for FITC and RITC, respectively.

EXAMPLE 1

Immunoprecipitation of HN:F. The existence of an HN:F complex was tested by cross-linking and coprecipitation experiments.

Figure 1:
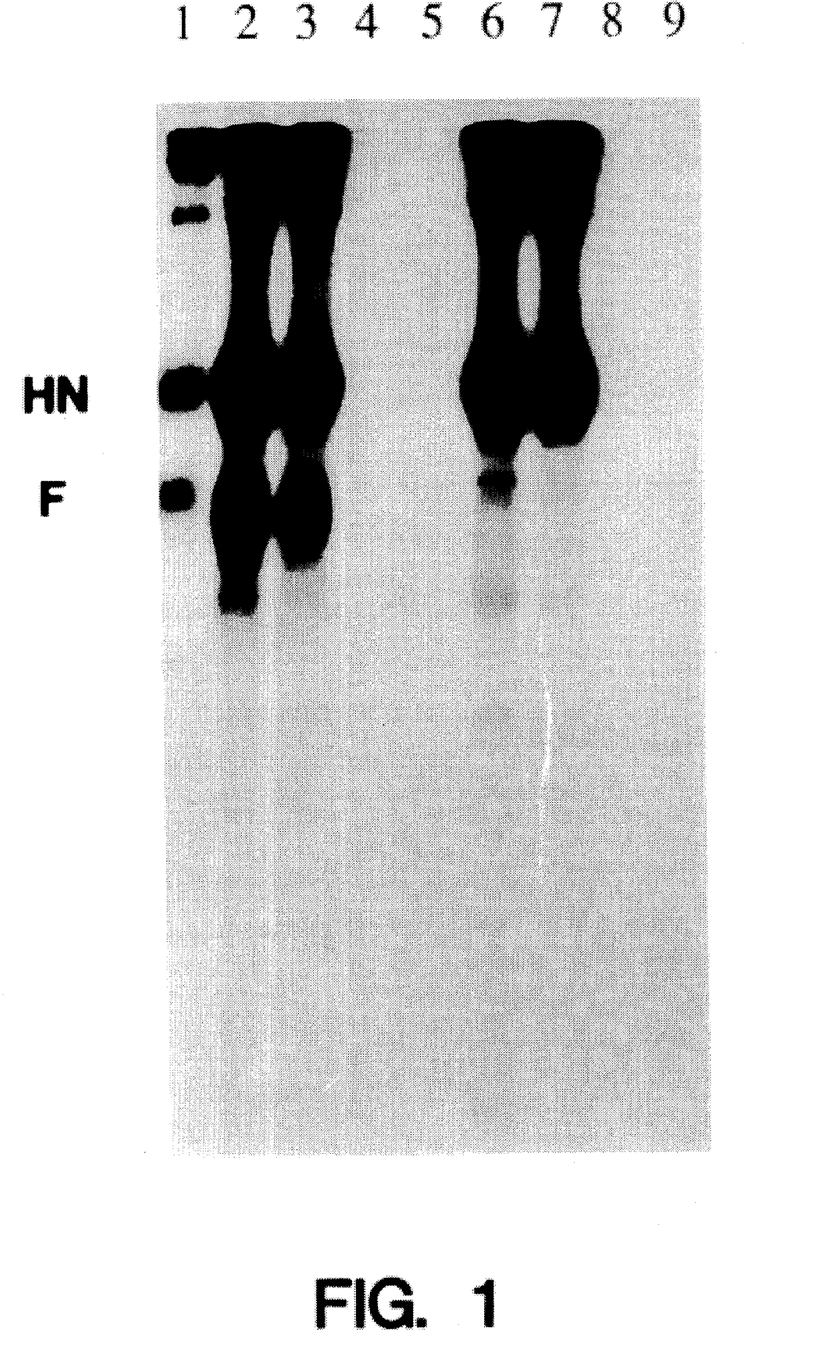
FIG. 1 shows SDS-PAGE separations of labeled proteins in the cross-linking/coprecipitation experiment described in Example 1. The positions of HN and F glycoproteins are indicated on the left. Lane numbers are indicated at the top.

HeLa-T4 cells were transfected with PI2-F and HN (see FIG. 1, lanes 1 to 3); PI2-F (FIG. 1, lanes 4 and 5); PI2-HN (FIG. 1, lanes 6 and 7) or infected with VV-T7 (FIG. 1, lanes 8 and 9). Cells were labeled [$^{35}$S]-methionine for 1 hr at 37° C. 12 hr posttransfection. Cross-linking was performed by incubating cells with 5 mM dithiobissuccinimidyl-propionate (DPS) on ice for 30 min (FIG. 1, lanes 3, 5, 7, and 9). Cells were then lysed with lysis buffer (10 mM lauryl maltoside, 100 mM NaCl, 50 mM hepes, pH 7.3) and immunoprecipitated with rabbit anti-PI2 virus antiserum (lane 1) and rabbit anti-PI2 HN antiserum (lanes 2 to 9).

After treatment with the cross-linker DSP, the PI2-F and -HN proteins were found to be coprecipitated by rabbit antiserum to PI2-HN (FIG. 1, lane 3). In the absence of DSP, anti-PI2-HN antiserum also coprecipitated the PI2-F protein (FIG. 1, lane 2), suggesting that the F and HN proteins are strongly associated with each other. Under the same conditions, no F protein was found to be precipitated in the absence of HN (FIG. 1, lanes 4 to 9) and no nonspecific proteins were coprecipitated in the presence of the crosslinker DSP (FIG. 1, lanes 5, 7, and 9). Similar results were obtained under conditions using strong lysis buffer such as RIPA buffer.

EXAMPLE 2

Figure 2:
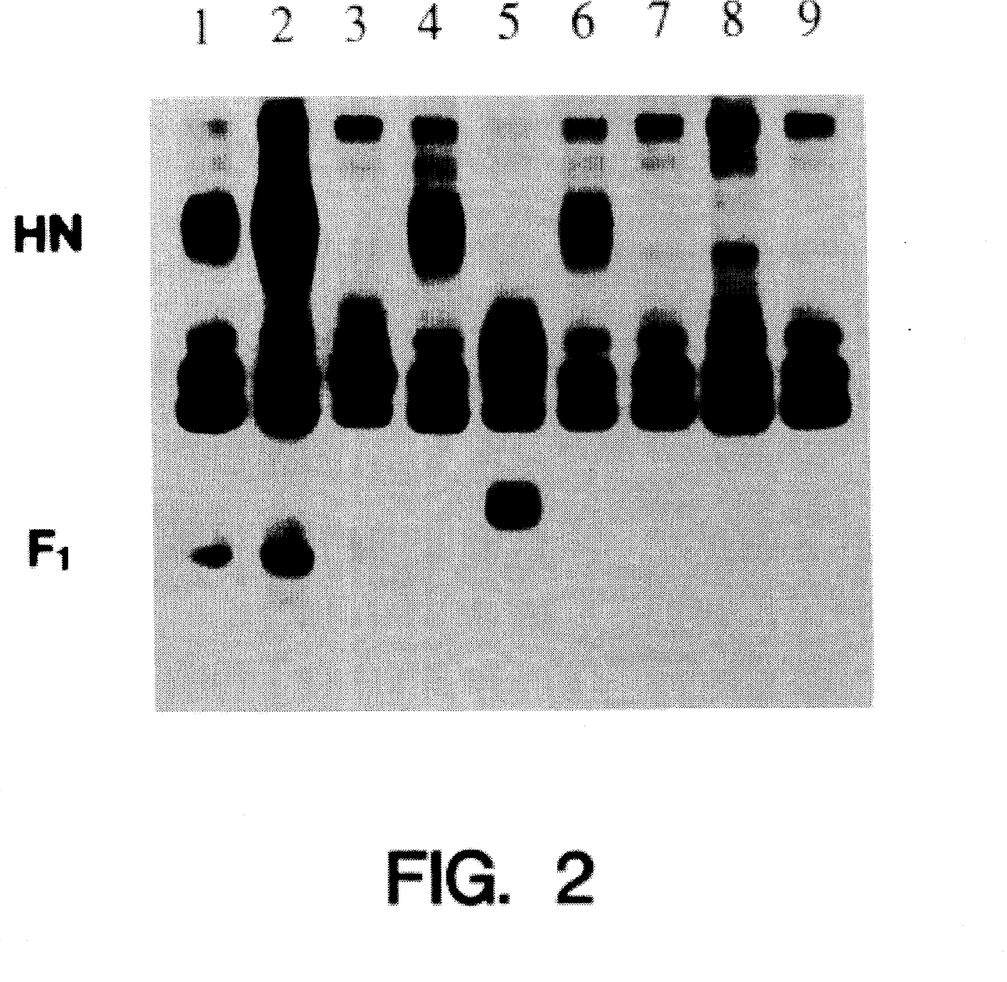
FIG. 2 shows SDS-PAGE separations of labeled proteins in the biotinylation and coprecipitation experiment described in Example 2. The positions of $F_1$ and HN are indicated at the left; lane numbers at the top of each lane.

Cell-surface location of HN:F complex. To investigate the interactions of the F and HN proteins on the cell surface, a biotinylation assay was employed to label the proteins on the cell surface. Results are shown in FIG. 2. HeLa-T4 cells were cotransfected with PI2-F and PI2-HN (lanes 1 and 2), SN F and SN HN (lane 3), SN F and PI2-HN (lane 4), SV5-F and SV5-HN (lane 5), SV5-F and PI2-HN (lane 6), or transfected with PI2-F (lane 7), SN F (lane 8) of SV5-F (lane 9). At 12 hr posttransfection cells were labeled with [$^{35}$S]-methionine for 3 hr at 37° C., surface proteins were biotinylated with NHS-SS-Biotin and then the biotinylated proteins were immunoprecipitated with rabbit anti-PI2 virus antiserum (lane 1), rabbit anti-PI2-HN antiserum (lanes 2, 4, 6 to 9), rabbit anti-Sendai virus antiserum (lane 3), or rabbit anti-SV5 antiserum (lane 5). One μg/ml trypsin was added to SN F-transfected cell medium during the labeling. Biotinlyated proteins were finally precipitated with Streptavidin agarose beads and analyzed by SDS-PAGE.

As shown in FIG. 2, the homologous F protein, PI2-F, was found to be coprecipitated by anti-PI2-HN antiserum (lane 2), whereas heterologous F proteins, SN F (lane 4) or SV5-F (lane 6), were expressed on cell surfaces but were not coprecipitated when coexpressed with PI2-HN and precipitated by PI2-HN antiserum. These results indicate that the PI2-F and HN proteins are physically associated with each other on cell surfaces, whereas heterologous combinations of F and HN do not show a similar association. Thus, the physical association of F and HN as revealed by the coprecipitation experiments parallels their functional interaction in the induction of cell fusion.

EXAMPLE 3

Figure 3A:
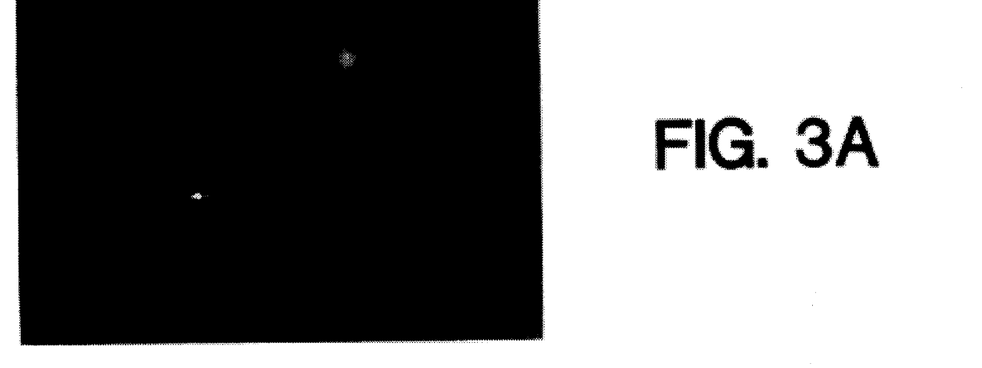
Figure 3B:
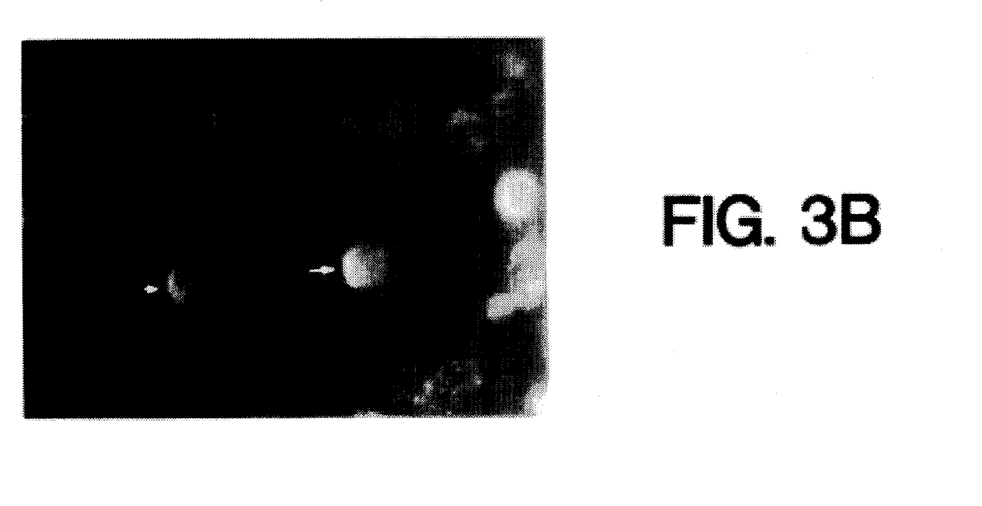

Type-homologous F and HN Glycoproteins were found to cocap on the cell surface. To further study the interactions of the F and HN proteins on the cell membrane, capping and cocapping assays were performed in HeLa cells which were infected with PI3 virus or doubly-infected with PI2 and PI3 viruses. As described in "Capping and Cocapping Assays," supra two aliquots of HeLa cells infected with PI3 virus were incubated with rabbit anti-PI3-HN antiserum at 0° C. for 30 min followed by incubation with FITC-conjugated secondary antibody (goat antirabbit IgG) at 37° C. or 0° C. for 30 min. The PI3-HN proteins were found to redistribute to form a unipolar cap when cells were incubated at 37° C. (FIG. 3A), whereas cells incubated at 0° C. showed random distribution of the PI3-HN proteins on the cell surface (data not shown). If under conditions facilitating capping (at 37° C.) of HN, the F proteins also form a cap at the same position (cocapping) on the cell surface, this would indicate that these two proteins are physically associated with each other since they move together laterally. Cocapping was therefore examined by double staining with FITC-labeling for the HN proteins and RITC-labeling for the F proteins, respectively. After cells were infected with PI3 virus for 12 to 16 hr, cells were incubated with rabbit anti-PI3-HN antiserum (at 0° C.) and FITC-conjugated goat antirabbit IgG (at 37° C.) for 30 min and 45 min, respectively, followed by incubation for 30 min with monoclonal antibody to PI3-F (at 0° C.) and RITC-conjugated goat antimouse IgG (at 0° C.). As indicated by the double exposure in FIG. 3B, on the surface of the doubly-stained cells the two membrane proteins were redistributed to form a unipolar cap in the same position; the RITC-stained PI3-F proteins were found to overlap the FITC-stained PI3-HN proteins.

Figure 3C:
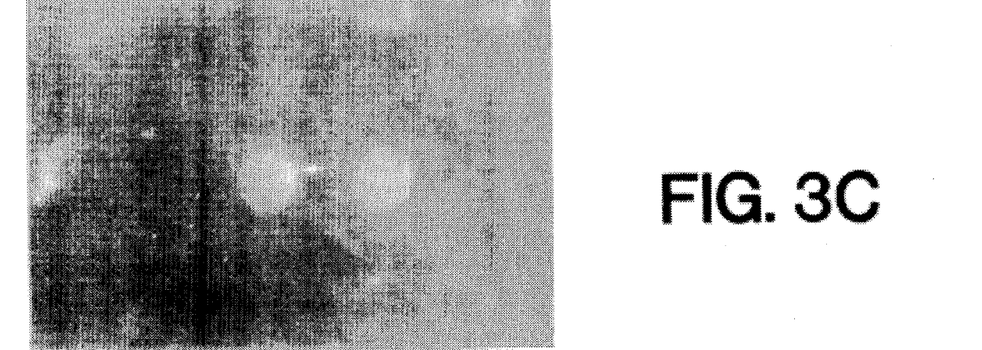

We also investigated the physical relationship between heterologous combinations of F and HN proteins on the cell surface by the capping assay. PI2 and PI3 virus-coinfected cells were incubated with rabbit anti-PI2-HN antiserum for 30 min at 0° C. and subsequently with FITC-conjugated goat antirabbit IgG for 45 min at 37° C. Then, cells were incubated with monoclonal antibody against PI3-F and RITC-conjugated goat antimouse IgG at 0° C. for 30 min, respectively. As shown in FIG. 3C, FITC-stained PI2-HN formed a cap while RITC-stained PI3-F remained uniformly distributed on the cell surface (shifted to the right in the double exposure). Coinfected cells which were doubly stained but incubated at 4° C. did not show capping (data not shown). These results further indicate that F and HN proteins of the same virus type are physically associated with each other and they can laterally move together on the cell surface under certain conditions, whereas heterologous F and HN proteins fail to show a similar association.

EXAMPLE 4

Specific antibodies to HN:F. Purified, partially purified or crude preparations of HN:F are used to immunize an animal or human to prepare polyclonal antibodies specific to HN:F complexes. Such preparations are also used to select for monoclonal antibodies specific for HN:F. Antibodies concurrently raised against contaminants in the HN:F preparation used for immunization are removed by standard antibody clearance techniques known in the art. Antibodies raised against a crude HN:F preparation from transfected HeLa-T4 membranes are cleared by reaction with similarly prepared membranes from cells transformed with vector only. Antibodies specific to the HN and F moieties only are similarly cleared by reaction with purified HN and F. [Standard techniques of immunization, antibody purification, and monoclonal antibody preparation are given in Harlow, E. and Lane, D., *Antibodies, A Laboratory Manual*, Cold Spring Harbor Laboratory, Cold Spring Harbor, N.Y. (1988)].

HN:F complexes have been shown herein to be stable to cell lysis conditions (Examples 1 and 2) which employ a mild detergent, lauryl maltoside. Adaptations of techniques previously employed for purifying HN and F [Ray, R. and Compans, R. (1987) *J. Gen. Virol.* 68:409–418] are applied to initial stages of purifying HN:F complex. Affinity chromatography using antibody as the affinity ligand is not employed, however, because the conditions used for elution disrupt the HN:F complex. The whole cell lysates of transfected cells can be used as a crude HN:F preparation, after dialysis to remove detergent and resuspension of membrane components. Alternatively, purified virus particles can be used as a source of HN:F. HN:F is further solubilized with octyl-D-glucoside or cholate and reconstituted into lipid vesicles [Ray, R. and Compans, R. (1987): Compans et al., U.S. Pat. No. 4,790,987]. Contaminating host cell proteins are removed by immunoprecipitation using antibodies to nontransformed host cells. Further purification can be carried out by affinity chromatography using a natural ligand of HN:F, e.g. sialic acid, as the affinity ligand. Elution can then be carried out under mild conditions such as a salt gradient that do not disrupt HN:F.

Immunization by HN:F, either alone or in combination with uncomplexed HN and F, provides protective immunity against infection by type-homologous virus. It will be understood that protection need not be complete to be of value. Protection is provided if, by any clinical signs or laboratory measurement related to disease severity, the normal course of disease in an infected animal or human patient is ameliorated. Indicia of protection include, but are not limited to, reduction in severity or duration of symptoms, reduction of virus titre from lungs, trachea or other tissues, reduction in histopathology, and the like. The use of HN:F as an immunizing antigen leads to production of antibodies to HN, F and HN:F. Since the latter is directly involved in tissue pathology and virus spread, antibodies against HN:F inhibit these activities and thereby contribute to and enhance the immunity conferred by HN and F as separate components.

Immunization by HN:F is carried out by techniques known and previously applied successfully in the art. In general, an immunologically effective amount of HN:F is administered to the animal or human to be immunized, either systemically or preferably intranasally. An immunologically effective amount is that amount sufficient to elicit an antibody response in the animal or human subject. For HN:F, an immunologically effective amount is comparable to the amounts already known for securing protection using uncomplexed HN and F.

A vaccine against a paramyxovirus strain contains as its principal ingredient HN:F in an immunologically effective amount, together with a physiologically acceptable carrier in which HN:F is either suspended or dissolved. Optionally, the vaccine can also include lipid to incorporate HN:F in lipid vesicles and an adjuvant to enhance intensity of the immune response. By using HN:F of a single virus type, protection is limited to infection by type-homologous viruses. Multivalent vaccines are prepared by incorporating HN:F of more than one virus type. By incorporating HN:F of PI1, PI2, and PI3, for example, a vaccine protective against all three virus types is produced. In addition, noncomplexed HN and F of one or more of the types can be included.

EXAMPLE 5

Vaccine Based on Anti-HN:F Antibodies. Protective immunity conferred by vaccines comprising HN, F, or both as the primary antigens, has been demonstrated for several paramyxovirus strains [Compans et al., U.S. Pat. No. 4,790, 987; Ray, R. et al. (1985) *J. Infect. Dis.* 152:1219–1230; Ray, R. et al. (1988) *J. Virol.* 62:783–787; Ray, R. et al. (1988) *J. Infect. Dis.* 157:648–654; Ray, R. et al. (1990) *J. Infect. Dis.* 162:746–749; Taylor, J. et al. (1991) *J. Virol.* 65:4263–4274]. These studies have further established that combined administration of HN and F provides greater protection than immunization with either HN or F singly [Ray et al. (1988) *J. Virol.*]. Immunization by intranasal administration of the antigens provides greater protection than systemic administration, suggesting that the more significant immunity is IgA-mediated [Ray et al. (1988) *J. Infect. Dis.*]. The immunity conferred is type-specific, or at least type-homologous-specific [Ray et al. (1990), supra]. In studies of children infected with PI3, the appearance of antibodies to HN and F correlated with protection from infection [Kasel, J. A. et al. (1984) *J. Virol.* 52:828–832]. Therefore, the results of successful immunization of animals render similar results predictable in the case of human immunization.

EXAMPLE 6

Peptide Mapping and Method of Selecting Antiviral Peptides. In order to identify the peptide domains of HN and F, which are critical for type-specific HN:F formation, a series of chimeric HN (or F) proteins is constructed. A chimeric HN protein is constructed having one or more segments obtained from PI2-HN and remaining segment(s) obtained from SV5-HN.

Figure 4:
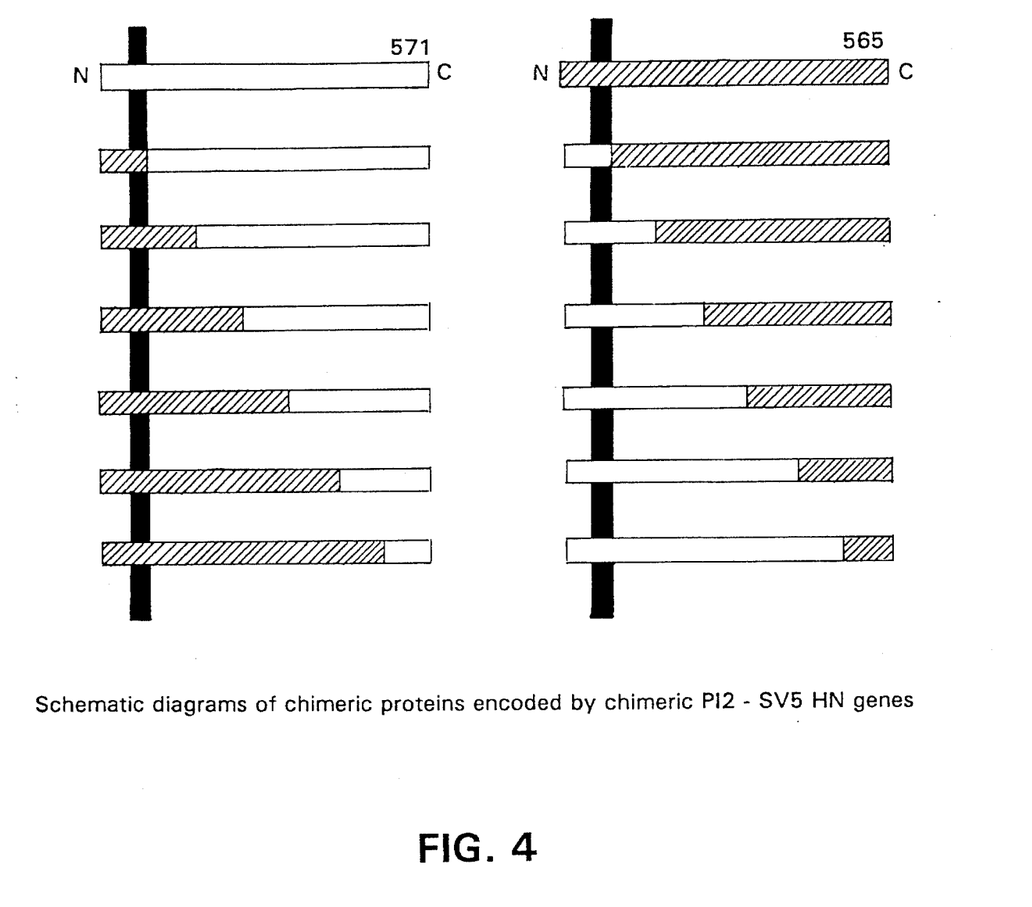
FIG. 4 is a schematic diagram of chimeric proteins encoded by chimeric PI2-SV5-HN genes. Each protein is represented by a bar reading left to right from N-terminal to C-terminal amino acid. The vertical black bar represents the position of the transmembrane region of each protein. Hatched regions represent regions of SV5-HN; open regions represent regions PI2-HN.

Because the PI2 and SV5-HN genes show a high level of sequence identity [Kawano et al., (1990) *Virology* 174:308–313; Hiebert et al., (1985) *J. Virol.* 54:1–6], initial studies are focused on these genes. To identify the regions of the HN protein that participate in type-specific fusion complex formation with the F Protein, a series of chimeric HN genes are constructed and expressed (see FIG. 4). This approach offers advantages over the alternative approach of introducing deletions into glycoprotein genes, because it seems less likely that one would encounter possible problems of incorrect folding with the chimeric molecules.

Figure 5:
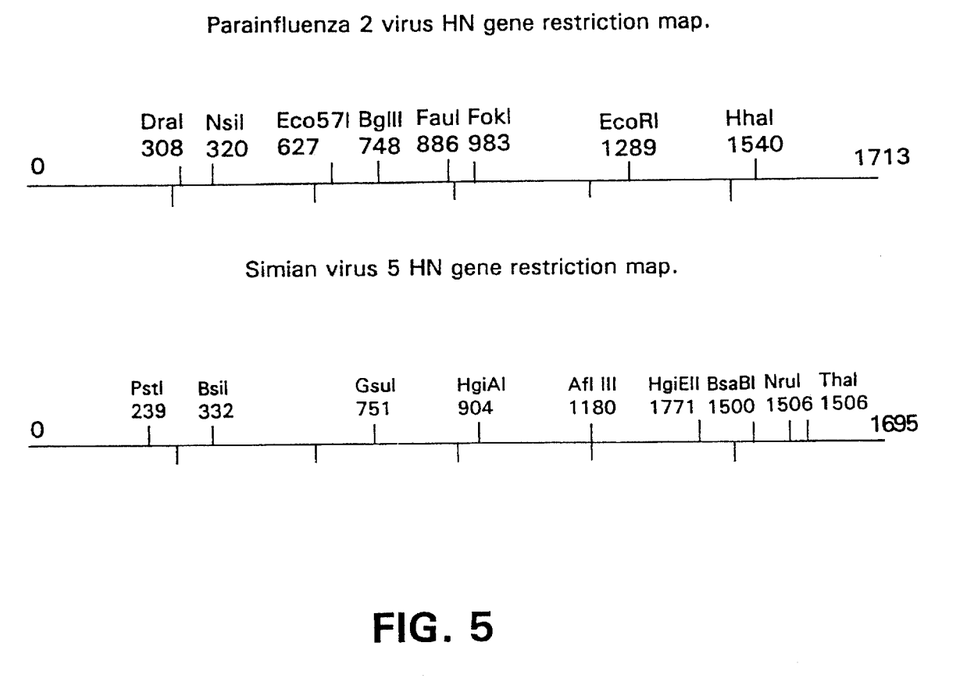
FIG. 5 shows restriction maps of the PI2-HN gene (upper line) and SV5-HN gene (lower line). Vertical lines show relative positions of restriction sites, as labeled. Numbers refer to the nucleotide position of the 5'-nucleotide at each cleavage site, numbered from the first A of the initiation codon.
Figure 6:
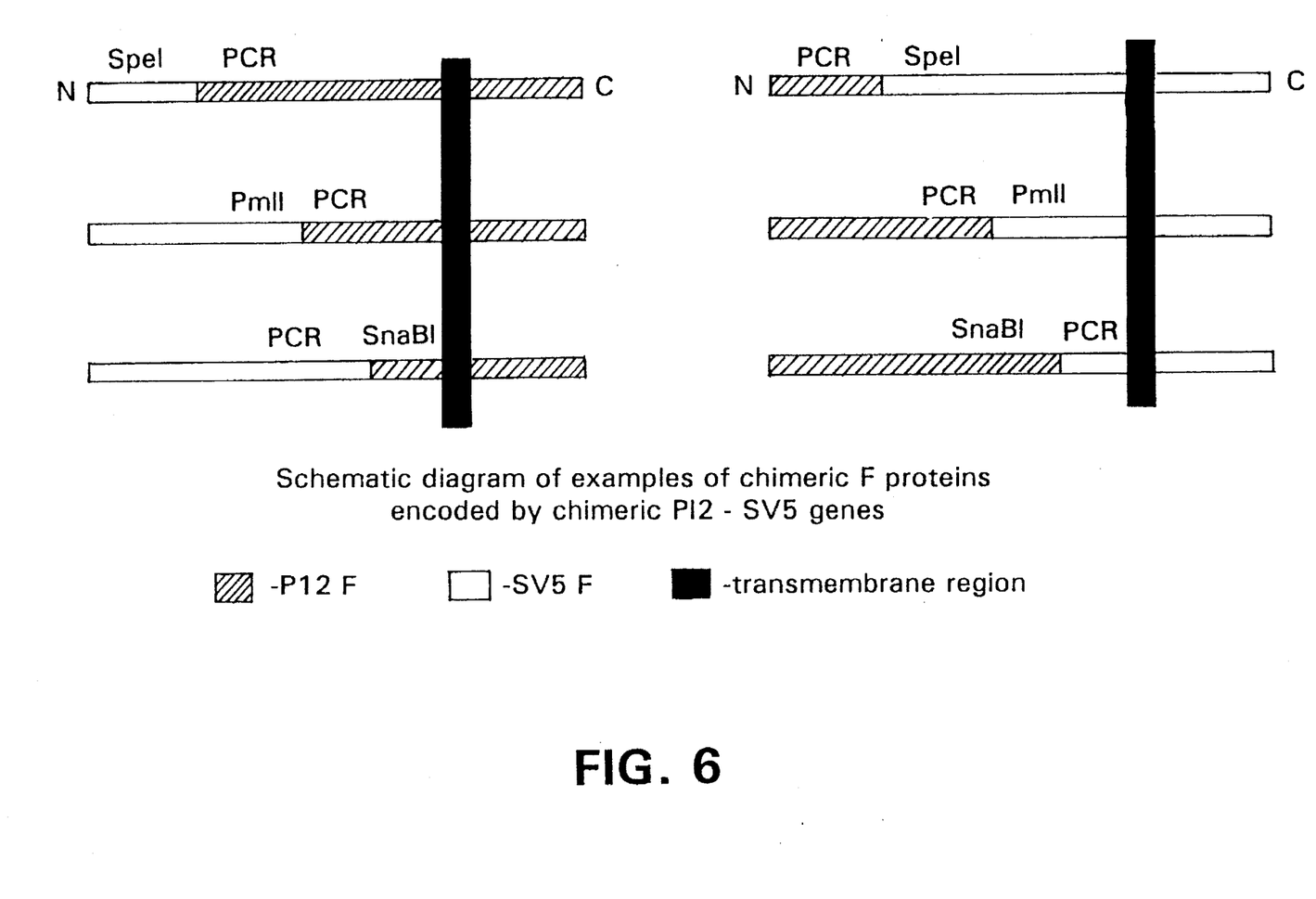
FIG. 6 is a schematic diagram of examples of chimeric F proteins encoded by chimeric PI2-SV5 genes. In this diagram, open bars designate regions of SV5-F protein; hatched bars designate regions of PI2-F protein. Representative restriction sites are shown, together with regions of PCR synthesis, as described in Example 6.

Sequences of the PI2-HN gene are sequentially replaced with sequences of the same regions from the SV5-HN gene. The PI2 and SV5-HN genes contain a number of appropriate single restriction sites to produce convenient DNA fragments (FIG. 5). The disulfide bonds in the two genes are conserved, so the chimeric proteins are considered to have similar folding properties.

Since in most cases the nucleotide sequence of one HN gene does not contain the same restriction site as the HN gene from the other virus, DNA fragments are synthesized by PCR with Pfu DNA polymerase (Stratagene, La Jolla, Calif.) that possesses proofreading activity resulting in a 12-fold increase in fidelity of DNA synthesis over Taq DNA polymerase. The oligonucleotide primers for PCR are designed to contain restriction sites for subsequent ligation. After purification by means of a "Geneclean II kit" (Bio 101, La Jolla, Calif.) DNA fragments from PI2 or SV5-HN genes are used to replace the corresponding fragments of the heterologous HN genes in the pGEM3 vector. The restriction endonuclease maps and DNA sequence of junction regions are determined to confirm the structures of chimeric genes.

HeLa T4 cells are used for protein expression studies and fusion assays since they are resistant to vaccinia-induced cytopathic effects [Matsuoka et al., (1988) *Virus Res.* 16:107–113]. Cells infected with the vaccinia virus-T7 recombinant (vv-T7) [Fuerst et al., (1986) *Proc. Nat. Acad. Sci. USA* 83:8122–8126] at a multiplicity of infection of 10 are transfected with 5–10 µg of plasmid DNAs, using lipofectin (TM GIBCO-BRL, Gaithersburg, Md.). After 12 to 20 h incubation at 37° C., cells are analyzed for protein expression by radiolabeling and immunoprecipitation. Cells are labeled with [$^{35}$S] methionine (100 µCi/ml) in methionine-free medium at appropriate time points posttransfection. Cells are lysed with cell lysis buffer (50 mM Tris-HCl, pH 7.5, 0.15 M NaCl, 1% Triton X-100, 0.1% SDS, 20 mM EDTA) and then analyzed by SDS-PAGE [Laemmli, (1970) *Nature* 227:680–685]. To ensure that each expressed protein is transport-competent, cell surface expression is monitored by surface immunofluorescence staining. Cells are grown on glass coverslips and vv-T7 infection and plasmid transfection are performed as described above. At appropriate time points, cells are washed with PBS, fixed with 1% paraformaldehyde in PBS for 5 min at room temperature, and examined by indirect immunofluorescence using polyclonal antibodies against PI2 or SV5-HN proteins and an appropriate fluorescent conjugate. In addition, the biological activity of the chimeric proteins is evaluated by hemadsorption and neuramindase assays. After ensuring that chimeric HN proteins are expressed and transported to the cell surface, they are then coexpressed with the wild-type PI2 or SV5-F proteins to examine whether the fusion-promotion activity is altered. To study the influence of HN on membrane fusion, HeLa T4 cells are infected with vaccinia-T7 recombinant [Fuerst et al., (1986), supra] and later are cotransfected with plasmid DNAs encoding the wild type F protein from PI2 or SV5 and chimeric or mutant HN protein genes using lipofectin. At 18 hr posttransfection the number of nuclei in 50 fused cells and the number of syncytia in 10 different fields of view are counted to determine the average size of syncytia and the frequency of cell fusion. Values obtained after transfection of the vector alone are subtracted. After the initial regions of HN important for interaction with F proteins are determined, chimerics in which smaller regions are exchanged are constructed and tested to further delineate the regions which are critical for fusion.

By analyzing which chimeric HNs form HN:F complex with PI2-F or PI3-F, one is able to map the region or regions within the HN amino acid sequence that contribute to type specificity, and to identify the sequence domains that participate in binding between HN and F.

To investigate the interactions of the F and HN on the cell surface, a biotinylation assay is employed to label the proteins on the cell surface [Lisanti et al., (1989), supra]. Cells are transfected with chimeric HN and either PI2 or SV5-F genes, metabolically labeled with $^{35}$S-methionine. Cell surface proteins are biotinylated with NHS-SS-Biotin (Pierce, Rockford, Ill.). After cells are lysed, samples are immunoprecipitated with specific antibodies to HN or F solubilized and then precipitated with streptavidin agarose beads (Pierce, Rockford, Ill.) to isolate the cell surface glycoproteins followed by SDS-PAGE analysis. One will thus determine whether the glycoproteins on cell surfaces are coprecipitated by antibody to one or the other glycoprotein. The results are compared with or without cross-linking. These results should indicate which chimeric HN proteins form complexes with either PI2 or SV5-F proteins.

The association of the two proteins on the cell surface can also be examined by a capping assay. It has been shown that viral glycoproteins can redistribute on the cell surface in response to multivalent antibody [Joseph and Oldstone, (1974) *J. Immunol.* 113:1205–1209]. If F and HN are closely associated, both molecules form a unipolar cap in the same position after incubation with specific antibody to one or the other protein. For this experiment, one uses antibodies produced in different animal species in order to distinguish the two proteins with appropriate conjugated second antibodies. The F and HN proteins are HeLa cells and at an appropriate time point cells are suspended, incubated with rabbit anti-HN antibody for 30 min at 0° C. and subsequently with FITC-conjugated goat antirabbit IgG for 45 min at 37° C. During the incubation period at 37° C., HN is redistributed into a cap structure on a significant fraction of cells. Cells are then incubated with mouse MAb against F and RITC-conjugated goat antimouse IgG at 0° C. for 30 min and individual cells are examined for fluorescein and rhodamine fluorescence to determine whether the F protein has redistributed to the same position. Similar experiments are using SV5-F instead of PI2-F. This provides an alternative approach for detecting the interaction of HN and F on cell surfaces.

In order to map the domains of the F protein that interact with the HN protein, chimeric genes between PI2 and SV5-F genes are similarly constructed and expressed. Sequences of one of the F genes are progressively replaced with the sequences of the same regions of the other F gene (FIG. 6). These studies complement the proposed studies of the HN gene.

The chimeric F proteins are then coexpressed with HN from PI2 or SV5 wild type viruses to examine whether their fusogenicity is altered. Once the area(s) important for interaction with HN are determined, chimerics with smaller domains are constructed and further tested. Regions with clustered amino acid changes related with fusion activity found in previous studies are focused on first. Site specific mutagenesis is used to precisely define the changes in particular amino acids involved in F-HN interaction.

Site-directed mutagenesis studies. After localization of the fusion-promotion region of PI2 and SV5-HN proteins, the next step is to determine the precise amino acid residues involved in interaction with the F protein for formation of an active fusion complex. After alignment, the amino acid sequences of HN proteins from the fusion promotion regions of PI2 and SV5 are compared and specific amino acids that differ between PI2 and SV5-HN proteins will be identified. For example, there are 3 short regions of amino acids inside the first 50 amino acid residues of the ectodomain that are similar between SN and PI1-HN and different for PI2 and SV5-HN. There are single cleavage sites for PstI, BglI and SspI restriction endonucleases near these regions of the SV5-HN gene so the introduction of point mutations into SV5-HN gene is facilitated.

To study the role of individual amino acid residues in fusion complex formation, site-specific mutagenesis by polymerase chain reaction (PCR) is used. Synthetic oligonucleotide primers for Pfu DNA polymerase (Stratagene, La Jolla, Calif.) are designed and synthesized (Novosibirsk Institute of Bioorganic Chemistry, Russia) to incorporate appropriate restriction sites as well as point mutations in primers used to amplify DNA fragments. Following PCR, the amplified fragments are cleaved by treatment with appropriate restriction endonucleases, and used to replace the corresponding segment of HN in a plasmid vector. Double mutants are generated from the first mutant by the same approach. Triple mutants are generated from the double mutant, and so on [McGinnes et al., (1993) *Virology* 196:101–110]. Thus, SV5 sequences are progressively replaced with PI2 sequences or vice versa. After sequencing to confirm the presence of the desired mutation(s), mutated HN genes are expressed from pGEM3 vectors transfected into vv-T7 -infected HeLa T4 cells.

To determine the effect of such mutation(s) on the interaction with F protein, HeLa T4 cells are cotransfected with mutant HN and wild-type F genes of SV5 or PI2 and the level of syncytia formation is quantitated in comparison with wild-type HN protein expression. Interaction of F and HN proteins to form complexes is evaluated by immune precipitation and cocapping as described above.

Fusion inhibition by synthetic peptides from fusion promotion regions. Peptides approximately 10–12 residues in length from regions of PI2-HN involved in membrane fusion are synthesized, purified by HPLC, and their solubility determined. When the interacting domains are present on the external surfaces of the cell, addition of peptides to the culture medium after transfection with PI2-F and HN genes results in competitive inhibition of F-HN interaction and membrane fusion. To assess the effect of peptides from the fusion-promotion region on F and HN interaction, synthetic peptides (0.1–200 μg/ml) are added to culture media after transfection with F and HN genes. Determination of the fusion frequency and the average size of giant cells are done as described above. When the interactions occur between intracellular portions of the F and HN molecules, one can prepare derivatized peptides to enhance peptide permeability.

The penetration of virus particles into cells also involves a membrane fusion process which is similar to the cell-to-cell fusion occurring later during virus infection. Thus, an inhibitor which prevents cell fusion also prevents virus replication. To measure inhibition of virus replication, peptide inhibitors which prevent fusion are incorporated at various concentrations into the agar overlay of plaque assays for PI2 virus on monolayers of Vero cells [Ray et al., (1989) *Virus Res.* 12:169–180]. The stage of infection at which inhibitors act is determined by addition of the inhibitors at various times postinfection during a single cycle of virus growth in LLC MK2 cells. Similar approaches are employed for inhibitors targeted to SV5 proteins.

To measure directly that synthetic peptides prevent the formation of complexes between F and HN, one examines the effect of peptides on formation of complexes assayed by immune precipitation or cocapping experiments as described above.

Studies with other paramyxoviruses. The steps set forth above focus on parainfluenza virus type 2 and SV5 because SV5 is the virus most closely related to PI2. However, it will be understood that one can extend this approach to other paramyxoviruses. In particular, human parainfluenza virus types 1 and 3 are both important causes of respiratory infection, and new approaches for their control are of great importance.

The invention as described herein is applicable throughout the range of paramyxoviruses, as will be understood from the knowledge that HN and F proteins or their counterparts are common features of all paramyxoviruses and have common functions in the infection process. Although the invention has been disclosed with reference to HN:F expressed in certain cell lines and isolated by certain means, the invention includes HN:F without regard to source cells and without regard to method of purification, although it will be understood that more highly purified forms of HN:F are generally less likely to contain undesired contaminants and interfering substances and are therefore generally preferred.

We claim:

1. A method for measuring the amount of an HN:F complex having a first component which may be HN or F and a second component which is F if the first component is HN, or HN if the first component is F, formed in the membrane of a transfected host cell expressing type-homologous paramyxovirus HN and F proteins, comprising the steps of:

a) separating from membrane-associated proteins of the cell a specific fraction consisting essentially of an HN:F complex and a first component of the HN:F complex; and b) measuring independently the amount of the second component of the HN:F complex in the specific fraction, whereby the amount of an HN:F complex formed in membranes of transformed host cells is measured.

2. The method of claim 1 wherein the second component is measured by an immunoassay using a labeled antibody to the second component of the HN:F complex.

3. The method of claim 1 further comprising the steps of:

prior to step a) incubating the cell in the presence of a labeled amino acid or amino acid precursor;

prior to step b) separating the first and second components of the HN:F complex by SDS-PAGE; and comparing the amount of label incorporated into the first component with the amount incorporated into the second component in the specific fraction, thereby measuring the amount of HN:F complex formed relative to the amount of the first component formed.

4. The method of claim 3 wherein the second component is measured by an immunoassay using a labeled antibody to the second component of the HN:F complex.

* * * * *